(12) United States Patent
Aranyi

(10) Patent No.: US 8,821,514 B2
(45) Date of Patent: Sep. 2, 2014

(54) POWERED TACK APPLIER

(75) Inventor: Ernest Aranyi, Easton, CT (US)

(73) Assignee: Covidien LP, Mansfield, MA (US)

( * ) Notice: Subject to any disclaimer, the term of this patent is extended or adjusted under 35 U.S.C. 154(b) by 321 days.

(21) Appl. No.: 12/773,034

(22) Filed: May 4, 2010

(65) Prior Publication Data

US 2010/0312257 A1 Dec. 9, 2010

Related U.S. Application Data

(60) Provisional application No. 61/184,920, filed on Jun. 8, 2009.

(51) Int. Cl.
| *A61B 17/00* | (2006.01) |
| *A61B 17/068* | (2006.01) |
| *A61B 17/064* | (2006.01) |
| *A61B 19/00* | (2006.01) |

(52) U.S. Cl.
CPC ..... *A61B 17/068* (2013.01); *A61B 2017/00734* (2013.01); *A61B 17/064* (2013.01); *A61B 2017/00017* (2013.01); *A61B 2017/00398* (2013.01); *A61B 2017/0648* (2013.01); *A61B 2019/301* (2013.01)
USPC ...................................... 606/139

(58) Field of Classification Search
CPC ................. A61B 2017/0649; A61B 2019/301; A61B 2019/303; A61B 2019/306
USPC ............. 606/142, 139, 143; 227/175.1–175.4
See application file for complete search history.

(56) References Cited

U.S. PATENT DOCUMENTS

| 37,165 A | 12/1862 | Gary |
| 3,079,606 A | 3/1963 | Bobrov et al. |
| 3,209,754 A | 10/1965 | Brown |
| 3,273,562 A | 9/1966 | Brown |
| 3,490,675 A | 1/1970 | Green et al. |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |

(Continued)

FOREIGN PATENT DOCUMENTS

| EP | 0 537 570 B1 | 4/1993 |
| EP | 0 647 431 A2 | 4/1995 |

(Continued)

OTHER PUBLICATIONS

European Search Report dated Apr. 17, 2007 for Corresponding Patent Application EP06026840.

(Continued)

*Primary Examiner* — Corrine M McDermott
*Assistant Examiner* — Shaun L David

(57) ABSTRACT

The present disclosure is directed to a fastener applying surgical fastener applier for ensuring proper seating of a fastener within tissue. The surgical fastener applier includes an actuation mechanism, a drive mechanism, and a control system. The control system is configured to determine loading along an axis and to allow movement of the drive mechanism.

23 Claims, 6 Drawing Sheets

(56) References Cited

U.S. PATENT DOCUMENTS

| | | | |
|---|---|---|---|
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Goldman et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | DelMedico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girnes |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,395,030 A | 3/1995 | Kuramoto et al. |
| 5,395,033 A | 3/1995 | Byrne et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,545,148 A | 8/1996 | Wurster |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A * | 9/1997 | Hooven ........................ 606/151 |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Videl et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,824,008 A * | 10/1998 | Bolduc et al. ................. 606/143 |

(56) References Cited

U.S. PATENT DOCUMENTS

| | | |
|---|---|---|
| 5,829,662 A | 11/1998 | Allen et al. |
| 5,830,121 A | 11/1998 | Enomoto et al. |
| 5,830,221 A | 11/1998 | Stein |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,517,565 B1 | 2/2003 | Whitman et al. |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnsude et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Millimam et al. |
| 6,959,852 B2 | 11/2005 | Shelton et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,059,508 B2 | 6/2006 | Shelton et al. |
| 7,077,856 B2 | 7/2006 | Whitman |
| 7,083,075 B2 | 8/2006 | Swayze et al. |
| 7,097,089 B2 | 8/2006 | Marczyk |

(56) References Cited

U.S. PATENT DOCUMENTS

| | | |
|---|---|---|
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Jorzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smirh et al. |
| 7,422,136 B1 | 9/2008 | Marczyk |
| 7,464,846 B2 | 12/2008 | Shelton, IV et al. |
| 2002/0025891 A1 | 2/2002 | Colosky et al. |
| 2002/0103489 A1 | 8/2002 | Ku |
| 2002/0111641 A1 | 8/2002 | Peterson et al. |
| 2002/0165541 A1 | 11/2002 | Whitman |
| 2003/0009195 A1 | 1/2003 | Field et al. |
| 2003/0073981 A1 | 4/2003 | Whitman et al. |
| 2003/0114851 A1 | 6/2003 | Truckai et al. |
| 2003/0120306 A1 | 6/2003 | Burbank et al. |
| 2003/0139746 A1 | 7/2003 | Groiso |
| 2004/0094597 A1 | 5/2004 | Whitman et al. |
| 2004/0232199 A1 | 11/2004 | Shelton, IV et al. |
| 2004/0232201 A1 | 11/2004 | Wenchell et al. |
| 2005/0006429 A1 | 1/2005 | Wales et al. |
| 2005/0006430 A1 | 1/2005 | Wales |
| 2005/0006431 A1 | 1/2005 | Shelton, IV et al. |
| 2005/0006434 A1 | 1/2005 | Wales et al. |
| 2005/0010236 A1 | 1/2005 | Frister |
| 2005/0023324 A1 | 2/2005 | Doll et al. |
| 2005/0067458 A1 | 3/2005 | Swayze et al. |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0131390 A1 | 6/2005 | Heinrich et al. |
| 2005/0139636 A1 | 6/2005 | Schwemberger et al. |
| 2005/0145674 A1 | 7/2005 | Sonnenschein et al. |
| 2005/0177176 A1 | 8/2005 | Gerbi et al. |
| 2005/0178813 A1 | 8/2005 | Swayze et al. |
| 2005/0187576 A1 | 8/2005 | Whitman et al. |
| 2005/0192609 A1 | 9/2005 | Whitman et al. |
| 2005/0228341 A1 | 10/2005 | Edgerley |
| 2005/0247753 A1 | 11/2005 | Kelly et al. |
| 2006/0000867 A1 | 1/2006 | Shelton, IV et al. |
| 2006/0022014 A1 | 2/2006 | Shelton, IV et al. |
| 2006/0022015 A1 | 2/2006 | Shelton, IV et al. |
| 2006/0049229 A1 | 3/2006 | Milliman et al. |
| 2006/0097025 A1 | 5/2006 | Milliman et al. |
| 2006/0151567 A1 | 7/2006 | Roy |
| 2006/0175375 A1 | 8/2006 | Shelton, IV et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0029364 A1 | 2/2007 | Kruszynski et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0084896 A1 | 4/2007 | Doll et al. |
| 2007/0084897 A1 | 4/2007 | Shelton, IV et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Ortiz et al. |
| 2007/0125826 A1 | 6/2007 | Shelton, IV |
| 2007/0152014 A1 | 7/2007 | Gillum et al. |
| 2007/0158385 A1 | 7/2007 | Hueil et al. |
| 2007/0175947 A1 | 8/2007 | Ortiz et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV |
| 2007/0175953 A1 | 8/2007 | Shelton, IV |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV |
| 2007/0175958 A1 | 8/2007 | Shelton, IV |
| 2007/0175959 A1 | 8/2007 | Shelton, IV |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0187453 A1 | 8/2007 | Smith et al. |
| 2007/0219563 A1 | 9/2007 | Voegele |
| 2007/0265640 A1 | 11/2007 | Kortenbach et al. |
| 2007/0278277 A1 | 12/2007 | Wixey et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0110957 A1 | 5/2008 | McBride et al. |
| 2008/0135600 A1 | 6/2008 | Hiranuma et al. |
| 2008/0164296 A1 | 7/2008 | Shelton et al. |
| 2008/0169329 A1 | 7/2008 | Shelton et al. |
| 2008/0185419 A1 | 8/2008 | Smith et al. |
| 2008/0281336 A1* | 11/2008 | Zergiebel ............... 606/142 |
| 2009/0001129 A1 | 1/2009 | Marczyk |
| 2009/0076534 A1 | 3/2009 | Shelton, IV et al. |

FOREIGN PATENT DOCUMENTS

| | | | |
|---|---|---|---|
| EP | 0 738 501 | A1 | 10/1996 |
| EP | 1 813 203 | A | 8/2007 |
| WO | WO 97/29694 | | 8/1997 |
| WO | WO 97/40760 | A1 | 11/1997 |
| WO | WO 99/52489 | A1 | 10/1999 |
| WO | WO 03/030743 | A2 | 4/2003 |
| WO | WO 03/045467 | | 6/2003 |
| WO | WO 2004/032760 | A2 | 4/2004 |
| WO | WO 2007/030753 | A2 | 3/2007 |
| WO | WO 2007/118179 | A2 | 10/2007 |

OTHER PUBLICATIONS

International Search Report for corresponding PCT Application—PCT/US06/21524—Date of Mailing May 28, 2008 (4 Pages).

Detemple, P., "Microtechnology in Modern Health Care", *Med Device Technol.* 9(9):18-25 (1998).

European Search Report for corresponding EP 08252703.7 dated Oct. 31, 2008 (3 pages).

European Search Report dated Feb. 27, 2009 for Corresponding Patent Application 08253184.9.

European Search Report for corresponding EP 08252703.7 dated Oct. 31, 2008 (7 pages).

European Search Report for corresponding EP 10 25 1047 application, date of completion is Dec. 1, 2010 (3 pages).

* cited by examiner

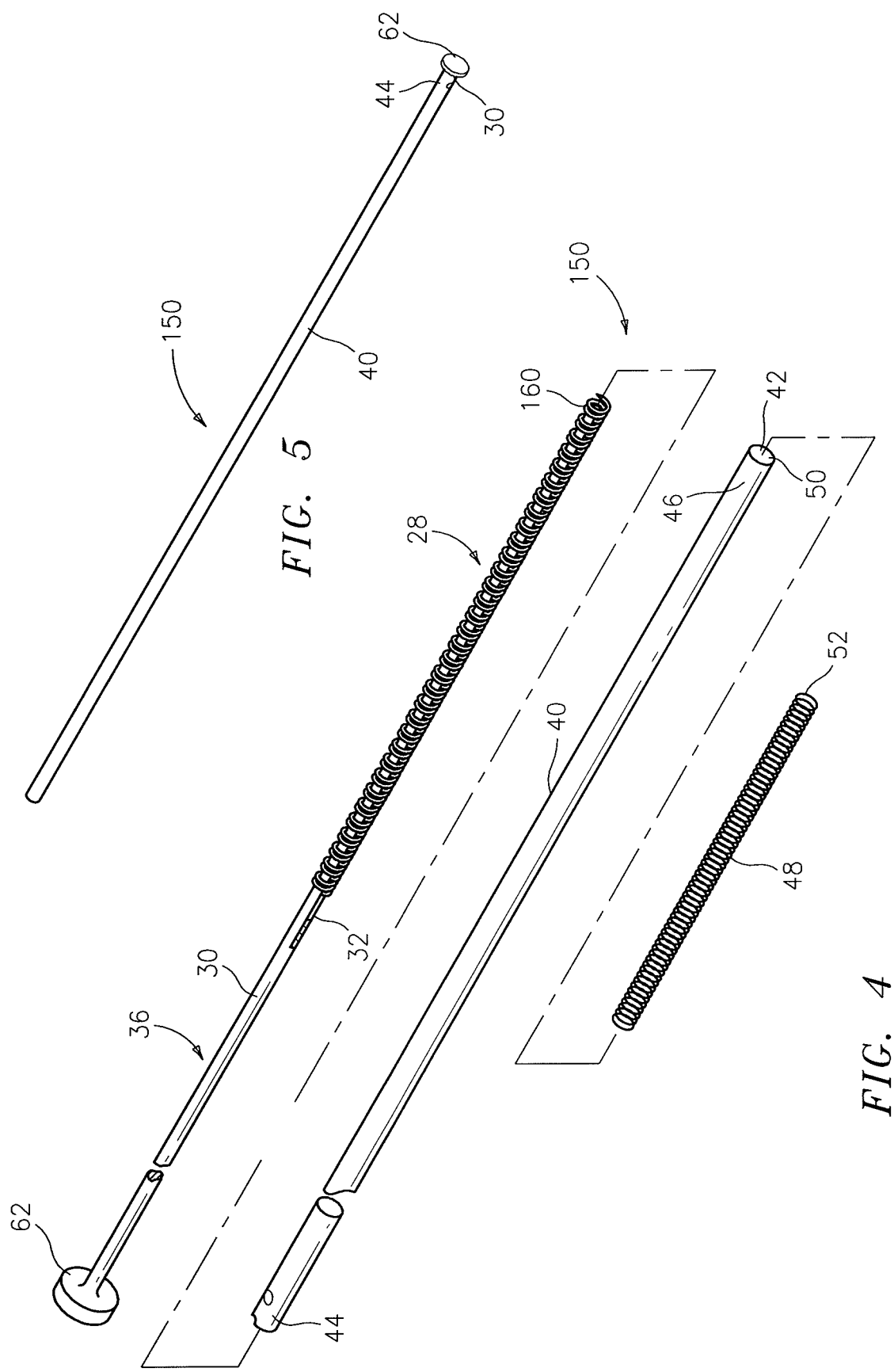

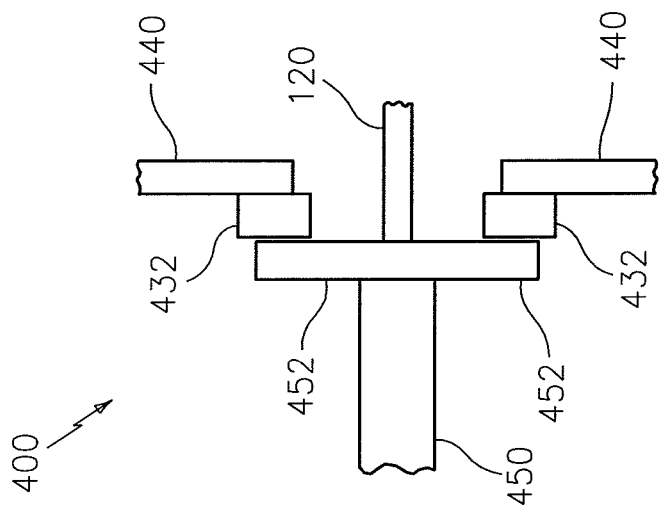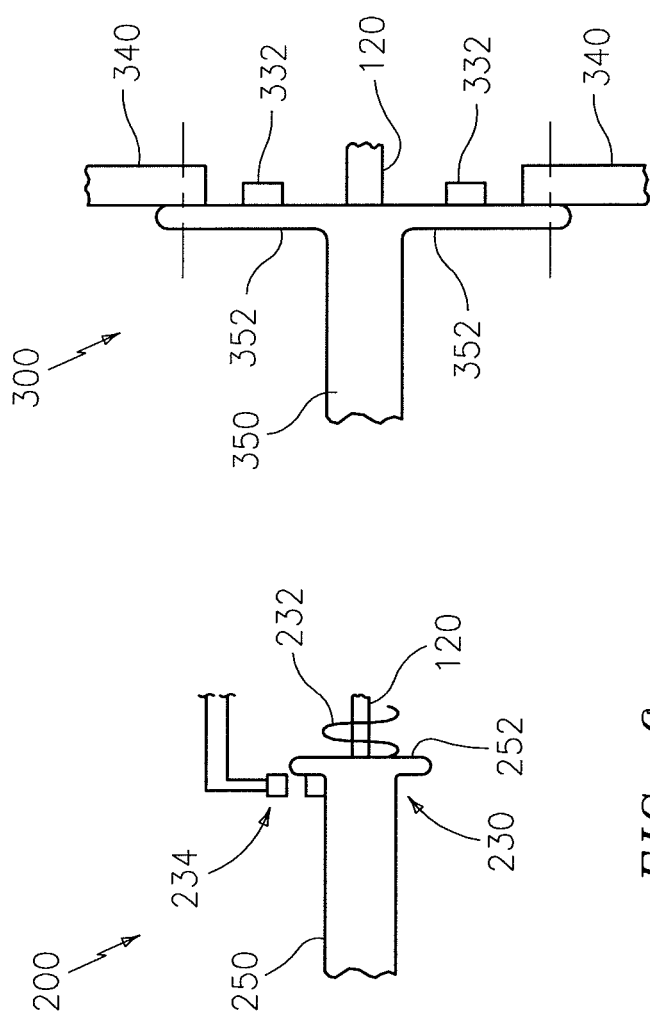
FIG. 6
FIG. 7
FIG. 8

POWERED TACK APPLIER

CROSS REFERENCE TO RELATED APPLICATION

The present application claims the benefit of and priority to U.S. Provisional Application Ser. No. 61/184,920 filed on Jun. 8, 2009, the entire contents of which are incorporated herein by reference.

BACKGROUND

1. Technical Field

The present disclosure relates to a device and a method of use thereof, for ensuring proper seating of a fastener during a surgical procedure. More particularly, the present disclosure relates to a fastener applying surgical fastener applier adapted for measuring a load applied to the surgical fastener applier and delaying operation of the surgical fastener applier until the applied load reaches a predetermined value.

2. Background of Related Art

Fasteners have been used surgically to eliminate the need for suturing, which is both time consuming and inconvenient. In many applications, the surgeon can use a stapler apparatus, i.e., a fastener-implanting device loaded with surgical fasteners to accomplish in a few seconds what would have taken many minutes to perform by suturing. This reduces blood loss and trauma to the patient.

Conventional surgical fasteners have been in the form of ordinary metal staples, which are bent by the delivery apparatus to hook together body tissue. Typically, conventional staples comprise a pair of legs joined together at one end by a crown. The crown may be a straight member connecting the legs or may form an apex. Moreover, the legs may extend substantially perpendicular from the crown or at some angle therefrom. Irrespective of the particular configuration, however, conventional staples are designed so that they may be deformed to hold body tissue.

Since conventional staples require deformation and must cooperate with applicators having an anvil or other means to deform the staples, conventional applicators typically comprise complex structures and can be prohibitively expensive. Conventional applicators must embody structure functioning to not only eject the fasteners but to do so in a manner so that the fastener deforms properly and timely.

Two part fasteners have also been conventionally utilized, where a barbed staple is used in conjunction with a retaining piece to hold the staple in place. Typically, the two part staple comprises a crown or backspan and two barbed prongs which are engaged and locked into a separate retainer piece. In use, the staple is pressed into the body tissue so that the barbs penetrate the tissue and emerge from the other side where they are then locked into the retainer piece. Retainers prevent the staple from working loose from the tissue. The two piece fasteners cannot be unlocked and are not removable.

Like other conventional applications, however, the two piece fasteners require the staple delivery apparatus to have access to both sides of the tissue. Thus, as with the other conventional applications, two piece fasteners are limited since they cannot be used where access to tissue is from one direction only.

In those situations where access to body tissues is limited to one direction, as in grafting procedures, deformable surgical fasteners have been conventionally employed. As mentioned previously, however, the applicators commonly used in these situations embody an anvil cooperating with a fastener to deform it and consequently, tend to be of a complex design.

Advancements have been made in this area so that applicators functioning to attach grafts to tissue, for instance, are not required to embody an anvil and may, therefore, have a more simple design. In particular, fasteners with threads or barbs are used where access to tissue is available in only on direction, thereby eliminating the need for deforming the fastener. These fasteners require the fastener applier to be placed firmly and perpendicular to the tissue to ensure proper placement.

SUMMARY

The present disclosure provides a surgical fastener applier capable of applying fasteners, having an actuation mechanism, a drive mechanism, and a control system. The actuation mechanism initiates movement of the drive mechanism through the controller. The controller is capable of determining the force, or load, applied to the distal end of the elongate member, or fastening portion, of the surgical fastener applier. The controller allows the drive mechanism to function when the load reaches a predetermined level.

The surgical fastener applier includes a handle with an elongate member partially extending therefrom. The drive mechanism is partially encapsulated by the handle and extends at least partially through the elongate member. A radial protrusion transfers the load applied to the distal end of the elongate member to a load measuring device. The load measuring device may include, but is not limited to, any conventional means, such as: a load cell, a spring, a sensor, and a strain gauge.

The drive mechanism is connected with a fastening portion to eject a fastener from the surgical fastener applier. The surgical fastener applier may include one or more fasteners within a cartridge detachably coupled to the drive mechanism. The drive mechanism may include a motor and a power supply. The same or different power supply may also be connected with the control system. The power supply may be an external source or by an internal battery.

As the distal end of the elongate member contacts tissue, the elongate member reacts by being placed in compression and transferring the load into the load measuring device of the control system. The load measuring device determines the force being applied and transferred along the elongate member. Once a predetermined load has been reached, the control system allows the drive mechanism to operate.

In another embodiment, the control system has a series of load measuring devices arranged about the elongate member. The control system is able to determine if the load is equally distributed about the distal end of the elongate member and allows the drive mechanism to operate once a predetermined load is equally distributed about the elongate member.

BRIEF DESCRIPTION OF THE DRAWINGS

The accompanying drawings, which are incorporated in and constitute a part of this specification, illustrate embodiments of the disclosure, and together with a general description of the disclosure given above, and the detailed description of the embodiments given below, serve to explain the principles of the disclosure.

FIG. 4 is a perspective view, with parts separated, of an elongate tubular portion, in accordance with the principles of the present disclosure;

FIG. 5 is a perspective view of an elongate tubular portion with a drive rod inserted, in accordance with the principles of the present disclosure;

FIG. 6 is a schematic partial cross-sectional view of the surgical fastener applier for applying fasteners, illustrating another embodiment of the control system;

FIG. 7 is a schematic partial cross-sectional view of the surgical fastener applier for applying fasteners, illustrating yet another embodiment of the control system;

FIG. 8 is a schematic partial cross-sectional view of the surgical fastener applier for applying fasteners, illustrating yet another embodiment of the control system.

Figure 1:
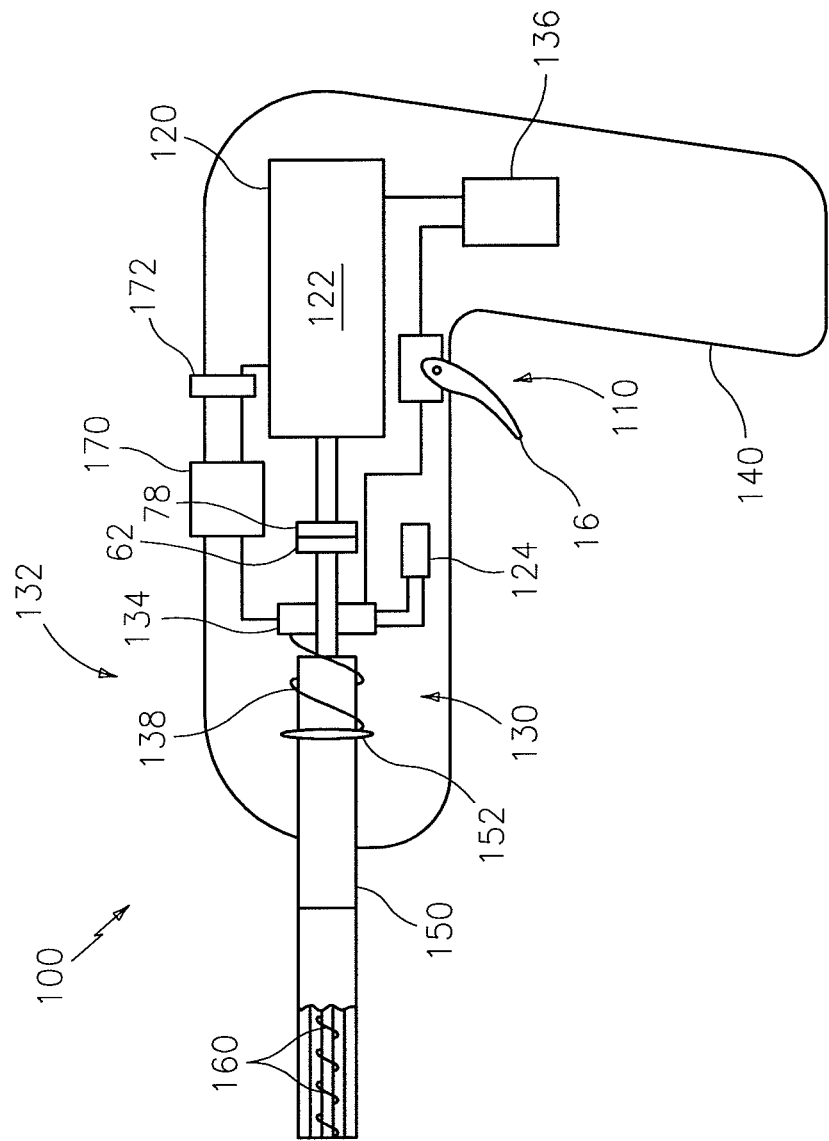
FIG. 1 is a schematic partial cross-sectional view of one embodiment of a surgical fastener applier for applying fasteners.

Other features and advantages of the present disclosure will become apparent from the following detailed description, taken in conjunction with the accompanying drawings, which illustrate, by way of example, the principles of the present disclosure.

DETAILED DESCRIPTION OF THE EMBODIMENTS

In the drawings and in the description which follows, the term "proximal", as is traditional, will refer to the end of the apparatus which is closest to the operator, while the term "distal" will refer to the end of the apparatus which is furthest from the operator.

The present disclosure can be used with any fastening device known in the art and is intended to encompass the same, shall be discussed in terms of both conventional and endoscopic procedures and apparatus. However, use herein of terms such as "endoscopic", "endoscopically", and "endoscopic portion", among others, should not be construed to limit the present disclosure to an apparatus for use only in conjunction with an endoscopic tube. The apparatus of present disclosure may find use in procedures in these and other uses including, but not limited to, where access is limited to a small incision, such as in arthroscopic and laparoscopic procedures, or other conventional medical procedures.

Referring now to the figures, wherein like reference numerals identify similar structural elements of the subject disclosure, there is illustrated in FIG. 1 a self-contained, powered, surgical fastener applier constructed in accordance with an embodiment of the subject disclosure and designated generally by reference numeral 100. Surgical fastener applier 100 is provided to apply fasteners to tissue or to secure mesh to tissue during surgical procedures such as hernia repair. The surgical fastener applier 100 is a surgical instrument that is intended, in one embodiment, to be disposable. However, the disposable arrangement is non-limiting and other non-disposable arrangements may be contemplated and are within the scope of the present disclosure.

The surgical fastener applier 100 includes an actuation mechanism 110, a drive mechanism 120, and a control system 130. The drive mechanism 120 is partially housed within a housing, generally represented by reference numeral 140. The housing 140 defines a series of internal chambers or spaces for supporting various mechanical components of the surgical fastener applier 100.

Figure 2:
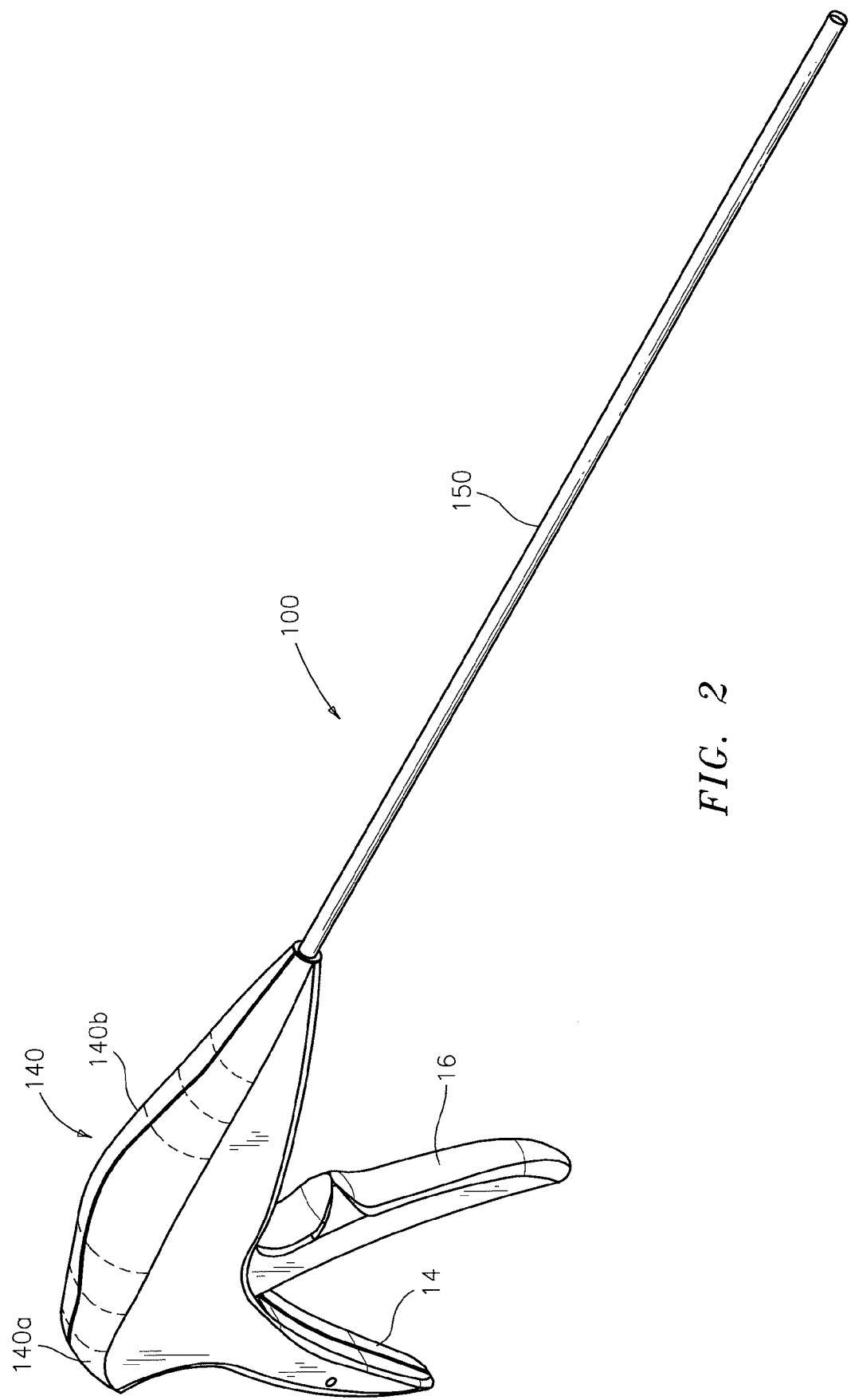
FIG. 2 is a perspective view of a surgical fastener applier, in accordance with the principles of the present disclosure.

Referring now to FIG. 2, housing 140 is formed as two separate housing halves 140a and 140b. A handle portion 14 extends from housing 140. A trigger 16 is movably mounted to the actuation mechanism and extends from the housing 140. Trigger 16 is pivotally connected to housing 140 with a free end of trigger 16 spaced from a free end of handle portion 14. Surgical fastener applier 100 also includes an elongated tubular portion 150 extending distally from housing 140. The elongated tubular portion 150 is provided to retain a plurality of fasteners for application to body tissue.

Figure 3:
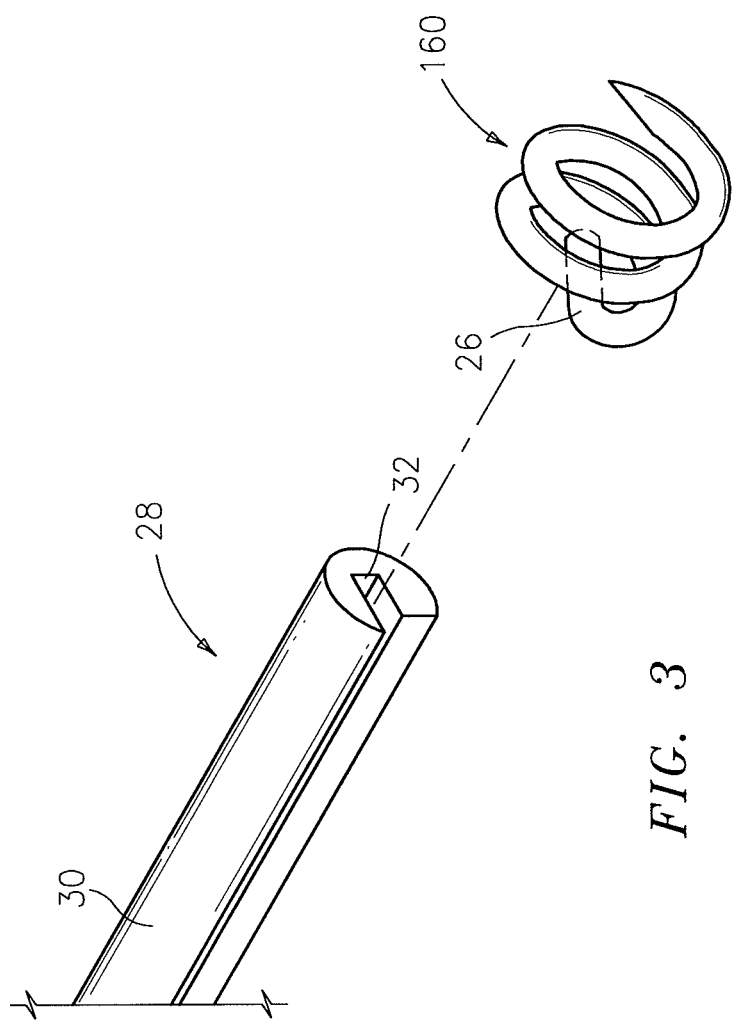
FIG. 3 is a perspective view of a distal end of a drive rod, in accordance with the principles of the present disclosure.

Referring now to FIG. 3, there is illustrated a fastener 160 suitable for use with surgical fastener applier 100. Fastener 160 is designed to be applied to tissue by rotating the fastener 160 into and through the tissue.

Concerning the material of the fastener 160, it is contemplated that the fastener be made from semi-stiff implantable wire, such as titanium, wound into a helical shape. In alternate embodiments, the fastener 160 may comprise plastic or absorbable materials. Examples of materials that can be used in constructing the fastener 160 include titanium, titanium alloys, stainless steel, nickel, chrome alloys and any other biocompatible implantable metals. Other options for materials are liquid crystal polymers, HDPE, polyglycolic acid, and polyglycolid hydroxgacetic acid. Further, it may also be desirable to coat the fastener, or a portion thereof, with a biocompatible lubricious material that provides for easier delivery of the fastener into tissue.

A distal portion 28 of a drive rod 30 is provided to retain and drive fasteners 160. Distal portion 28 generally includes a longitudinally extending slot 32 extending along the length of distal portion 28. Slot 32 is provided to receive tang 26 of fastener 160 therein, such that upon rotation of drive rod 30, fastener 160 is similarly rotated.

Referring now to FIG. 4, and as noted above, elongated tubular portion 150 contains a plurality of fasteners 160 and structure to drive fasteners 160 into tissue. A proximal portion 36 of drive rod 30 is of a generally solid circular cross-section. As best seen in FIG. 5, elongated tubular portion 150 also includes a generally tubular sleeve 40 defining a bore 42 therethrough and having a proximal end 44 and a distal end 46. Drive rod 30 is freely rotatable within bore 42 of tubular sleeve 40. Proximal end 36 of drive rod 30 extends out of proximal end 44 of tubular sleeve 40 and is coupled to a first gear 62. First gear 62 is provided to rotate drive rod 30 to advance fasteners 160 through elongated tubular portion 150 and drive fasteners 160 into tissue.

First gear 62 forms a part of the drive mechanism 120 provided to rotate drive rod 30. Drive mechanism 120 additionally includes a second gear 78 configured to engage the first gear 62. Second gear 78 is attached to a motor 122 and the motor is attached to a power supply 124. A rotational sensor or timer is provided within the motor structure to prevent more than one fastener from being driven out of the surgical fastener applier 100.

In order to move successive fasteners 160 in a distal direction upon rotation of drive rod 30 there is provided a spring 48, which is preferably braised or welded to an inner surface 50 of tubular sleeve 40. Spring 48 creates a helical longitudinally extending surface 52 configured for engagement with the fasteners 160. Thus, upon rotation of drive rod 30 fasteners 160 are moved along surface 52 and through tubular sleeve 40.

Surgical fastener applier 100 additionally includes an actuation mechanism 110 which, in combination with drive mechanism 120, convert motion of trigger 16 into rotary motion of drive rod 30. Alternatively, a switch assembly or other means can also be used in place of the trigger.

The surgical fastener applier 100 has a control system 130. The control system 130 prevents the drive mechanism 120 from operating until an external load is applied to the distal end of the tubular sleeve 40. To determine the amount of force, or load, applied to the distal end of the tubular sleeve 40, the control system 130 has a load measuring device 132 and is connected to a power supply 136.

As the distal end of the tubular sleeve 40 contacts tissue, the tubular sleeve 40 is placed in compression and transfers the load to the proximal end of the tubular sleeve 40. As shown in FIG. 1, a radial protrusion 152 placed about the proximal end of the tubular sleeve 40 transfers the load to the load measuring device 132. The load measuring device 132 may include, but is not limited to, any conventional means, such as: a load cell, a spring, a sensor, and a strain gauge.

The load measuring device may be mechanical or electrical, or a combination thereof. An example of the combination of the mechanical and electrical is shown in FIG. 1. A spring 138, one component of the control system 130, is placed between the radial protrusion 152 and the housing 140 to place the tubular sleeve 40 in a proximal position. A force being applied at the distal end of tubular sleeve 40 moves the proximal end of tubular sleeve 40 proximally and into a sensor 134, or switch, another component of the control system 130, thereby activating the switch and causing a circuit to be completed, resulting in the activation of the motor 122. The load component 134 may further comprise a non-contact sensor.

The force required to be applied can be either preset at about 2 lbs or the operator can adjust the required load of the control system. The user can also adjust the control system to require the force to be in a particular range. Too much force indicates the presence of bone, which may break the fastener, causing the surgeon to spend crucial time retrieving the pieces of the broken fastener. By controlling the force applied upon the surgical fastener applier, the surgeon has the ability to control the compression of the tissue at the surgical site and to prevent breakage of the fastener.

The surgical fastener applier 100 provides the surgeon with an indicator 170. The indicator 170 may display an amount of load distribution and/or provide feedback of the status of the fastening, or display information as to where the drive screw is located and how far the drive screw is from actuating the drive mechanism 120, or any combination thereof, along with other information.

The indicator 170 may be any device that provides a sensory indication and is on an outer surface of the surgical fastener applier 100 in a location where the surgeon can readily observe the indicator. The indicator 170 may be any device that permits a visual, tactile, or audible monitoring of one or more conditions of the surgical fastener applier 100. As seen in FIG. 1, the indicator 170 is disposed on the housing 140. Alternatively, the indicator 170 may be disposed on the elongate tubular portion 150, on the trigger 16, or in any other suitable location where the indicator may be easily viewed by the surgeon.

The control system 130 may prevent firing of the fastener. However, in order to provide the proper feedback to the surgeon, the indicator 170 will provide the surgeon with the progress of the firing of the drive mechanism 120.

Still further, the surgical fastener applier 100 has an override switch 172. The override switch 172 is a manual or other switch that may selectively disengage the control system 130 to permit a direct actuation of the drive mechanism 120 by the actuation mechanism 110 without measuring the load disbursement.

The operation of surgical fastener applier 100 will now be described. In an initial or starting position, trigger 16 is biased away from handle 14. To actuate surgical fastener applier 100, trigger 16 is pivoted toward handle 14. Once the actuation mechanism 110 is engaged and a predetermined load has been applied to the tubular sleeve, the control system 130 allows the drive mechanism 120 to operate the motor 122 starts to rotate, in turn rotating second gear 78.

Upon rotation of second gear 78, the mating first gear 62 rotates drive rod 30 within tubular sleeve 40. As drive rod 30 is rotated within tubular sleeve 40, drive rod 30 rotates fasteners 160. Fasteners 160, being engaged with surface 52 of spring 48, are moved distally within tubular sleeve 40. Thus, rotation of drive rod 30 rotates or screws a fastener 160 out of the distal end 46 of elongated tubular portion 150. This rotation of drive rod 30 also moves a next successive fastener 160 into position to be applied to tissue during a next cycling of surgical fastener applier 100.

It should be noted that upon a complete depression of trigger 16, drive rod 30 is rotated precisely a predetermined amount such that only one fastener 160 is driven out of the distal end 46 of elongated tubular portion 150.

Once trigger 16 had been completely depressed and a fastener 160 has been driven from elongated tubular portion 150 into tissue mesh or other suitable structure, trigger 16 may be released. Trigger 16 is then biased to an open or initial position. After the surgical fastener applier 100 fires, the surgical fastener applier 100 or a portion thereof may be withdrawn from the body.

Even though it is disclosed herein that the surgical instrument is either electrically powered or manually operated, it is contemplated that the surgical fastener applier can be hydraulic, pneumatic, or fluid driven also. Also, the surgical instrument may include one or more fasteners within a cartridge ejectably coupled to the drive mechanism.

In another embodiment, as illustrated in FIG. 6, the elongate tubular portion 250, of surgical fastener applier 200, has a radial protrusion 252 to keep the spring 232 from sliding over the elongate tubular portion 250. The radial protrusion 252 may also be used to keep the elongate tubular portion 250 located between mounting points on the housing. The mounts allow the elongate tubular portion 250 to travel between a first distal position and a second proximal position, while preventing the elongate tubular portion 250 from rotating.

The spring 232 compresses at a constant rate that provides a predictable resistance to a force acting upon the distal end of the elongate tubular portion 250. Therefore, when the correct amount of force is transferred and acts upon the spring 232, the elongate tubular portion 250 will move relative to the housing and cause both portions of a sensor 234 to align. The alignment of both parts of the sensor 234 will cause the circuit to be completed and the drive mechanism 120 to urge a fastener from the surgical fastener applier 200.

In another embodiment, as shown in FIG. 7, the control system has a series of load measuring devices arranged about the elongate tubular portion. The surgical fastener applier 300 has a plurality of strain gauges 332 placed upon radial protrusions 352. The strain gauges are placed between the elongate tubular portion 350 and the mounting points to the housing 340. This configuration allows deflection along the radial protrusions 352 that can be measured using the strain gauges 332. A circuit (not shown) or micro-processor (not shown) are connected to the strain gauges 332 and is able to determine the loading based upon the deflection. Further, the radial protrusions 352 and strain gauges 332 may be placed in more than two directions about the elongate tubular portion 350 to ensure that the elongate tubular portion 350 is in pure compression. Thus, the control system is able to determine if the load is equally distributed about the distal end of the elongate tubular portion and allows the drive mechanism to operate once a predetermined load is equally distributed about the elongate tubular portion.

As seen in FIG. 8, in another embodiment, the surgical fastener applier 400 has load cells 432 placed at the mounting points of the radial protrusions 452 to the housing 440. The load cells 432 are connected with a processor (not shown). The processor prevents the operation of a drive mechanism 120 until a specified load is applied, or until a specified load is equally distributed about the elongate tubular portion 450.

Figure 9:
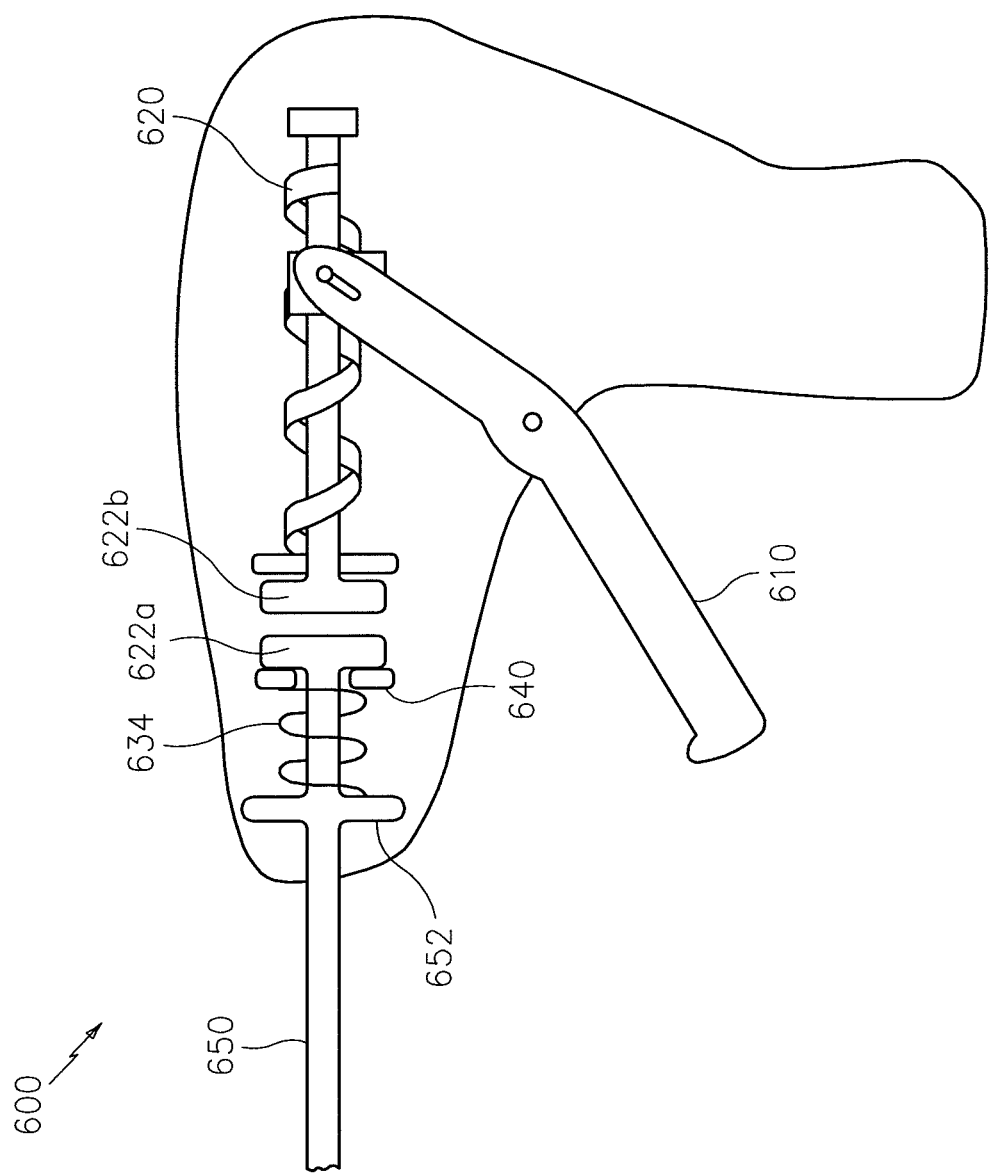
FIG. 9 is a schematic partial cross-sectional view of the surgical fastener applier for applying fasteners, illustrating yet another embodiment of the control system.

The drive mechanism can have either a manual or motorized operation. In another embodiment, surgical fastener applier 600 with a manual operation, discussed below and shown in FIG. 9, the actuation mechanism 610 is mechanically coupled to the drive mechanism 620. The linear motion of the actuation mechanism 610 causes the drive mechanism 620 to rotate. A spring 634 may be used as the control system in a surgical instrument without electrical power. As force is applied to the distal end of the elongate tubular portion 650, radial protrusions 652 force a spring to collapse and mating gears 622a, 622b are coupled together. The spring 634 may be coupled to the elongate tubular portion 650 and the housing 640 in a way that cause a space between mating drive members 622a, 622b until a sufficient force moves the mating drive members 622a, 622b and completes the geared coupling. Once the geared surface of mating drive member 622a connects with and engages the geared surface of mating drive member 622b the movement of the drive mechanism 620 is able to be transferred to the fastening portion of the surgical fastener applier 600.

As discussed herein, the tubular sleeve transfers the load to the control system, however, this is not meant to be a limitation. This is meant to serve as an example of how the present disclosure may be used and are not meant to be limiting. It is envisioned that the force be applied to a part of the drive mechanism and that the control system is configured to measure the loading of the drive mechanism. It is envisioned that other members of a fastener applier can be used to transfer the load to the control system. For example, a drive rod can extend beyond the elongate tubular portion. In this example the drive rod would be forced proximally from contact with the tissue and the control system is configured to measure amount of displacement. In another example, a separate member extends from the elongate tubular portion and is configured to be displaced in response to a load resulting from contact with tissue. A locator need can also be used to transfer the load applied by the tissue. The locator needle ensures that the preliminary functions are met and allows the locator needle to penetrate the tissue to create a guide hole. The locator needle also enables the mesh to be located and secured in place.

Other surgical fastener appliers for incorporation into surgical fastener applier 100 are also envisioned such as the surgical fastener applier disclosed in commonly assigned U.S. Pat. Nos. 5,830,221, 6,562,051, and 6,884,248 and U.S. application Ser. No. 10/517,402, filed Dec. 7, 2004, the entire contents of each being incorporated by reference herein.

Although being shown as an endoscopic surgical fastener applier, the present drive system may be used with any surgical fastener applier known in the art.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure. Those skilled in the art will envision other modifications within the scope and spirit of the claims appended hereto.

What is claimed:

1. A surgical fastener applier for ensuring proper seating of a fastener comprising:
   a housing;
   an actuation mechanism disposed in mechanical cooperation with the housing and defining a longitudinal axis;
   a rotatable center drive mechanism operatively associated with the actuation mechanism;
   a rotatable drive rod extending distally from the housing and configured to support a plurality of fasteners, the rotatable drive rod being at least partially radially surrounded by the plurality of fasteners;
   an axially translatable tubular sleeve coaxially disposed along at least a portion of the drive rod and configured to at least partially radially surround said plurality of fasteners; and
   a control system including a load measuring device supported in the housing, wherein the load measuring device is a load sensor, the control system being configured to prevent a motor of the drive mechanism from operation until a predetermined amount of an external load is directly applied to a distal portion of the tubular sleeve.

2. The surgical fastener applier of claim 1, wherein the tubular sleeve further comprises a radial protrusion, the radial protrusion positioned distally of the load measuring device and configured to transfer the external load to the load measuring device.

3. The surgical fastener applier of claim 1, wherein the drive mechanism extends at least partially through the tubular sleeve.

4. The surgical fastener applier of claim 1, wherein the load measuring device includes a component selected from a group consisting of a load cell, a spring, a sensor, a strain gauge, and a combination thereof.

5. The surgical fastener applier of claim 1, further comprising a power source operatively connected to the control system.

6. The surgical fastener applier of claim 1, wherein the drive mechanism has a motor.

7. The surgical fastener applier of claim 1, further comprising a power supply operatively connected to the drive mechanism.

8. The surgical fastener applier of claim 1, wherein the drive mechanism is configured to eject a fastener of said plurality of fasteners from the surgical fastener applier.

9. The surgical fastener applier of claim 8, further comprising a removable cartridge configured to hold the plurality of fasteners.

10. The surgical fastener applier of claim 1, wherein a distal most end of the tubular sleeve extends distally past a distal most end of the drive rod prior to said external load being applied to the tubular sleeve.

11. The surgical fastener applier of claim 1, wherein the rotatable drive rod is rotatable 360° about the longitudinal axis.

12. The surgical fastener applier of claim 1, wherein the rotatable drive rod includes a longitudinally-extending slot therein, wherein the slot is configured to receive a portion of each of the plurality of fasteners.

13. The surgical fastener applier of claim 1, wherein the rotatable drive rod simultaneously extends through each of the plurality of fasteners.

14. A surgical fastener applier for ensuring proper seating of a fastener comprising:
   a housing;
   an actuation mechanism disposed in mechanical cooperation with the housing and defining a longitudinal axis;
   a drive mechanism operatively associated with the actuation mechanism;
   a rotatable center drive rod extending distally from the housing and configured to support a plurality of fasteners, the rotatable drive rod being at least partially radially surrounded by the plurality of fasteners;
   an axially translatable tubular sleeve coaxially disposed along at least a portion of the drive rod and configured to at least partially radially surround said plurality of fasteners; and
   a control system including at least one load measuring device supported in the housing, wherein the load measuring device is a load sensor, the control system being configured to activate a motor to allow movement of the drive mechanism once a predetermined load is equally distributed about the distal end of the tubular sleeve.

15. The surgical fastener applier of claim 14, wherein the tubular sleeve further comprises a plurality of radially spaced protrusions.

16. The surgical fastener applier of claim 14, further comprising a power source operatively connected to the control system.

17. The surgical fastener applier of claim 14, wherein the drive mechanism has a motor.

18. The surgical fastener applier of claim 14, further comprising a power supply operatively connected to the drive mechanism.

19. The surgical fastener applier of claim 14, wherein the drive mechanism is configured to eject a fastener of said plurality of fasteners from the surgical fastener applier.

20. The surgical fastener applier of claim 14, wherein a distal most end of the tubular sleeve extends distally past a distal most end of the drive rod prior to the distal end of the tubular sleeve being subject to said predetermined load.

21. The surgical fastener applier of claim 14, wherein the rotatable center drive rod is rotatable 360° about the longitudinal axis.

22. The surgical fastener applier of claim 14, wherein the rotatable center drive rod includes a longitudinally-extending slot therein, wherein the slot is configured to receive a portion of each of the plurality of fasteners.

23. The surgical fastener applier of claim 14, wherein the rotatable center drive rod simultaneously extends through each of the plurality of fasteners.

* * * * *